(12) United States Patent
Takeoka et al.

(10) Patent No.: US 7,887,837 B2
(45) Date of Patent: Feb. 15, 2011

(54) DRUG DELIVERY MATERIAL

(75) Inventors: Shinji Takeoka, c/o School of Medicine, Keio University, 35, Shinanomachi, Shinjuku-ku, Tokyo 160-8582 (JP); Yousuke Okamura, Tokyo (JP); Ippei Maekawa, Tokyo (JP); Makoto Handa, Tokyo (JP); Yasuo Ikeda, Tokyo (JP)

(73) Assignee: Shinji Takeoka, Tokyo (JP)

( * ) Notice: Subject to any disclaimer, the term of this patent is extended or adjusted under 35 U.S.C. 154(b) by 184 days.

(21) Appl. No.: 12/087,424

(22) PCT Filed: Jan. 5, 2007

(86) PCT No.: PCT/JP2007/050011

§ 371 (c)(1),
(2), (4) Date: Aug. 14, 2008

(87) PCT Pub. No.: WO2007/077990

PCT Pub. Date: Jul. 12, 2007

(65) Prior Publication Data

US 2009/0220422 A1    Sep. 3, 2009

(30) Foreign Application Priority Data

Jan. 6, 2006    (JP) .............................. 2006-001916

(51) Int. Cl.
*A61K 9/127*    (2006.01)
(52) U.S. Cl. ....................................................... 424/450
(58) Field of Classification Search ................... 424/450
See application file for complete search history.

(56) References Cited

U.S. PATENT DOCUMENTS

| 6,177,059 B1 | 1/2001 | Matsuda et al. |
| 2003/0113262 A1 | 6/2003 | Ikeda et al. |
| 2003/0130190 A1* | 7/2003 | Hallahan et al. .............. 514/12 |

FOREIGN PATENT DOCUMENTS

| EP | 1 262 490 | * 4/2002 |
| EP | 1 591 451 | 11/2005 |

OTHER PUBLICATIONS

Chavakis et al, Journal of Biological Chemistry, vol. 278, No. 46, pp. 45375-45381, 2003.*
Suzuki-Inoue et al, Journal of Biological Chemistry, vol. 276, No. 2, pp. 1643-1652, 2001.*

(Continued)

*Primary Examiner*—Gollamudi S Kishore
(74) *Attorney, Agent, or Firm*—Wenderoth, Lind & Ponack, L.L.P.

(57) ABSTRACT

The present invention provides a drug delivery material, which is a conjugate of 1) a drug-carrying molecular assembly, 2) a linker and 3) a substance that recognizes activated platelet, injury site of blood vessel and/or inflammatory tissue, and capable of efficiently delivering a drug to a desired site, during which the drug under delivery does not affect sites other than a desired site (hence, low possibility of causing side effects), which releases the drug only at the desired site without requiring an external means and allows the drug to exhibit an effect.

21 Claims, 10 Drawing Sheets

OTHER PUBLICATIONS

Gursoy et al. "The inhibitory effect of liposome-encapsulated indomethacin on inflammation and platelet aggregation", J. Pharm, Pharmacol, vol. 40, pp. 53-54, Apr. 29, 1988.

Ogura, et al. "Occlusion of retinal vessels using targeted delivery of a platelet aggregating agent", British Journal of Ophthalmology, vol. 77, pp. 233-237, (1993).

Nishiya et al. "Interaction of platelets liposomes containing dodecapeptide sequence from fibrinogen", Thromb Haemost, vol. 91, pp. 1158-1167, (2004).

Khoobehi, et al. "Laser-Induced Experimental Vascular Occlusion Using Liposome-Encapsulated ADP", Lasers in Surgery and Medicine, vol. 12(6), pp. 609-614, (1992).

* cited by examiner glutamic acid
stearyl alcohol
p-toluenesulfonic acid

Glu2C18 85%

MAL-PEG-NHS (Mw=3400)

TEA
chloroform
room temperature,
12hr

MAL-PEG-Glu2C18 64%
n=71

H12-Cys-SH

DMF
room temperature,
12hr

H12-MAL-PEG-Glu2C18 47%
n=71

US 7,887,837 B2

DRUG DELIVERY MATERIAL

TECHNICAL FIELD

This application is a U.S. National Stage for International Application No. PCT/JP2007/050011 filed Jan. 5, 2007.

The present invention relates to a drug delivery material which is a conjugate of 1) a drug-carrying molecular assembly, 2) a linker and 3) a substance that recognizes activated platelet, injury site of blood vessel and/or inflammatory tissue. More particularly, the present invention relates to a drug delivery material useful as a prophylactic or therapeutic agent or diagnostic agent for a disease or a reagent, particularly as a platelet substitute or an antiplatelet agent.

BACKGROUND ART

Various glycoproteins (GP) are present on the surface of a platelet, and involved in the expression of platelet function. As such platelet glycoproteins, GPIb, GPIIb, GPIIIa, GPIIIb, GPIV, GPIX and the like are known. Of these, GPIb functions as a receptor of the von Willebrand factor (vWF). GPIb is a heterodimer having a molecular weight of 160,000, wherein α chain and β chain are disulfide-bonded.

Recently, platelet substitutes are known, which have a functional macromolecule (e.g., GPIb, a recombinant 45 kDa hydrophilic part of α chain (rGPIbα), GPIIb/IIIa and the like) bound with the surface of a certain micro particle. Of these, those having rGPIbα are expected to function as a platelet substitute since they show an adhesive action resulting from the interaction between rGPIbα and the vWF. On the other hand, those having GPIIb/IIIa are expected to function as a platelet substitute since they show a coagulating action resulting from the interaction between GPIIb/IIIa and fibrinogen and/or vWF.

In addition, as micro particles bound these functional macromolecules, lipid membrane such as vesicle and the like, human albumin or polymer thereof, human red blood cell and the like are known, and patent reference 1 describes rGPIbα-bound vesicle.

Also, there are some known to induce hematological coagulation by aiding the platelet activity remaining in the patient blood, rather than to function as a platelet substitute since it has a functional macromolecule on the platelet. For example, one that induces platelet aggregation by interacting with GPIIb/IIIa on the platelet is known. To be specific, a conjugate of a vesicle and a peptide containing dodecapeptide (H12) contained in the GPIIb/IIIa recognition site of fibrinogen bound thereto is described in non-patent reference 1.

Patent references 2 and 3 describe conjugates having a linker inserted between GPIb or dodecapeptide, and vesicle, and teach that the conjugates can be used as drug delivery materials for physiologically or pharmacologically effective drugs by accumulating the conjugates on the injury site of blood vessels.

In addition, non-patent reference 2 describes a vesicle carrying adenosine diphosphate (ADP). ADP is a substance known to induce platelet aggregation or thrombus formation. This vesicle releases ADP by laser irradiation and induces platelet aggregation.

However, none of the aforementioned references disclose a drug delivery material that spontaneously releases a drug only at a desired site to achieve a pharmacological effect.

While patent references 2 and 3 describe use of the conjugates described therein as drug delivery materials, they do not describe specific embodiments thereof. Furthermore, while non-patent reference 2 describes a vesicle carrying ADP, the vesicle requires an external means of laser irradiation for releasing ADP.

patent reference 1: JP-A-9-208599
patent reference 2: WO01/64743
patent reference 3: WO2004/069862
non-patent reference 1: T. Nishiya et al., Thromb Haemost, 91, 1158-67 (2004)
non-patent reference 2: B. Khoobehi et at., Lasers Surg Med., 12(6), 609-14, 1992

DISCLOSURE OF THE INVENTION

Problems to be Solved by the Invention

The present inventors aim to provide a drug delivery material capable of efficiently delivering a drug to a desired site, during which the drug under delivery does not affect sites other than a desired site (hence, low possibility of causing side effects), which releases the drug only at the desired site without requiring an external means and allows the drug to exhibit an effect.

Means of Solving the Problems

The present inventors have found that, by binding a particular molecular assembly carrying a drug with a linker and a substance that recognizes an activated platelet, an injury site of blood vessel and/or an inflammatory tissue, the drug can be efficiently delivered to a desired cell (e.g., activated platelet) and/or biological tissue (e.g., injury site of blood vessel or inflammatory tissue), and that the cell and/or biological tissue interact(s) with the drug-carrying molecular assembly via the substance bound therewith, which recognizes the activated platelet, the injury site of blood vessel and/or the inflammatory tissue at such desired site, whereby the drug-carrying molecular assembly is physically stimulated by the cell and/or biological tissue and releases the drug from the drug-carrying molecular assembly, thus allowing the drug to exhibit a desired effect only at a desired site, which resulted in the completion of the present invention.

The gist of the present invention is as follows.

[1] A drug delivery material which is a conjugate of 1) a drug-carrying molecular assembly, 2) a linker and 3) a substance that recognizes an activated platelet, an injury site of blood vessel and/or an inflammatory tissue.

[2] The drug delivery material of [1], wherein the drug-carrying molecular assembly is a lipid bilayer vesicle encapsulating the drug in an inner aqueous phase thereof.

[3] The drug delivery material of [1] or [2], which is represented by (a drug-carrying molecular assembly)-(a linker)-(a substance that recognizes an activated platelet, an injury site of blood vessel and/or an inflammatory tissue).

[4] The drug delivery material of [3], wherein the linker comprises an amphiphilic molecule that becomes a part of the constituent of the drug-carrying molecular assembly when bound therewith, and the linker is bound with the drug-carrying molecular assembly via said amphiphilic molecule.

[5] The drug delivery material of [3], wherein the linker comprises a hydrophobic molecule, and the linker and the drug-carrying molecular assembly are bound with the drug-carrying molecular assembly via said hydrophobic molecule.

[6] The drug delivery material of any of [1]-[5], wherein the linker comprises a spacer part.

[7] The drug delivery material of [6], wherein the spacer part is polyoxyethylene.
[8] The drug delivery material of any of [1]-[7], wherein the drug is selected from the group consisting of a platelet aggregation inducer, a platelet aggregation inhibitor, a vasoconstrictor, a vasodilator and an anti-inflammatory agent.
[9] The drug delivery material of any of [1]-[7], wherein the drug is selected from the group consisting of adenosine diphosphate, collagen, collagen-derived peptide, convulxin, serotonin, aspirin, dipyridamole, ticlopidine, cilostazol and beraprost.
[10] The drug delivery material of any of [1]-[9], wherein the substance that recognizes an activated platelet, an injury site of blood vessel and/or an inflammatory tissue is a substance that recognizes integrin or selectin, which is exposed on the activated platelet, collagen exposed on the injury site of blood vessel, a vWF bound with collagen exposed on the injury site of blood vessel, selectin exposed on the inflammatory tissue and/or a selectin ligand exposed on leukocyte, and is incorporated into an aggregate of the activated platelet and/or leukocyte, and/or accumulated on the injury site of blood vessel and/or the inflammatory tissue.
[11] The drug delivery material of [10], wherein the substance that recognizes the activated platelet, the injury site of blood vessel and/or the inflammatory tissue is selected from the group consisting of H12, GPIbα, GPIa/IIa, GPVI, MAC-1, fibrinogen, P-selectin and PSGL-1.
[12] The drug delivery material of [2], wherein the lipid bilayer vesicle consists of a mixed lipid comprising cholesterol in a molar ratio of 20-100% relative to phosphatidylcholine, which is hydrogenated egg yolk lecithin, hydrogenated soybean lecithin, distearoyl phosphatidylcholine or dipalmitoyl phosphatidylcholine, and the conjugate of the linker and the substance that recognizes an activated platelet, an injury site of blood vessel and/or an inflammatory tissue in a proportion of 0.001-20% relative to the phosphatidylcholine.
[13] The drug delivery material of [12], wherein the lipid bilayer vesicle has a particle diameter of 50-300 nm, and the lamellarity of the lipid bilayer is 1 to 4.
[14] A drug delivery material which is a conjugate of 1) a drug-carrying molecular assembly, 2) a linker and 3) a substance that recognizes an activated platelet, an injury site of blood vessel and/or an inflammatory tissue, wherein the drug is released from the drug-carrying molecular assembly with a physical stimulation from a cell or biological tissue when it reaches the cell or biological tissue.
[15] The drug delivery material of [14], wherein the cell is an activated platelet or leukocyte, and the drug is selected from the group consisting of a platelet aggregation inducer, a platelet aggregation inhibitor, a vasoconstrictor, a vasodilator and an anti-inflammatory agent.
[16] The drug delivery material of [14], wherein the biological tissue is an injury site of blood vessel or an inflammatory tissue, and the drug is selected from the group consisting of a platelet aggregation inducer, a platelet aggregation inhibitor, a vasoconstrictor, a vasodilator and an anti-inflammatory agent.
[17] A diagnostic agent comprising the drug delivery material of any of [1]-[16].
[18] A reagent comprising the drug delivery material of any of [1]-[16].
[19] A platelet substitute comprising the drug delivery material of any of [1]-[16].
[20] An antiplatelet agent comprising the drug delivery material of any of [1]-[16].

Effect of the Invention

Since the drug delivery material of the present invention does not coagulate with inactive platelet and the like in blood vessels to induce unnecessary formation of thrombus or intravascular coagulation of blood and the like before reaching the desired cell and/or biological tissue and, when it reaches said site(s), the drug-carrying molecular assembly is disintegrated only at the desired site to release the drug even without an external means such as laser and the like, the drug delivery material can efficiently and conveniently deliver the drug to the desired cell and/or biological tissue. As a result, the drug delivery material of the present invention shows high drug absorption efficiency, and can remarkably decrease the side effects.

BEST MODE FOR CARRYING OUT THE INVENTION

Figure 1:
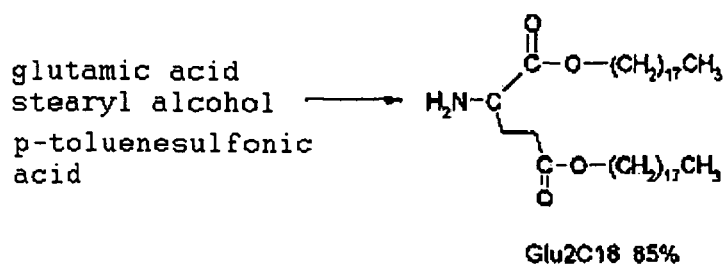
FIG. 1 shows a synthesis scheme of Glu2C18 and H12-MAL-PEG-Glu2C18 described in Example 1.
Figure 1:
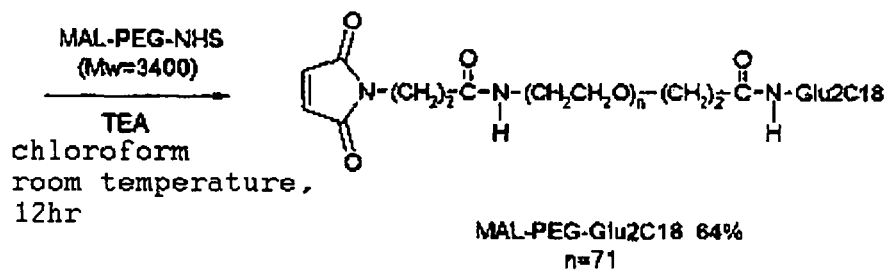
Figure 1:
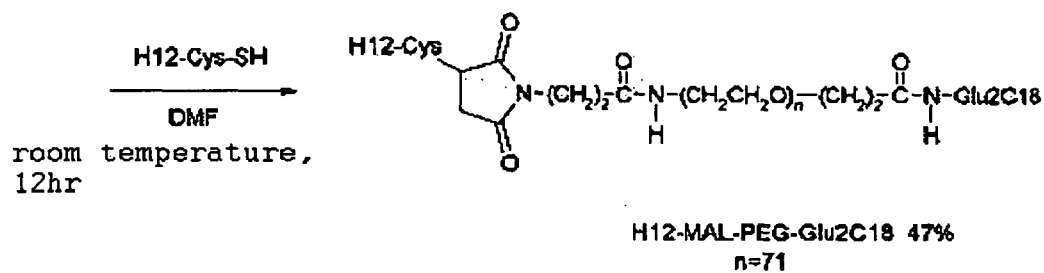

The present invention provides a drug delivery material which is a conjugate of 1) a drug-carrying molecular assembly, 2) a linker and 3) a substance that recognizes an activated platelet, an injury site of blood vessel and/or an inflammatory tissue (sometimes to be abbreviated as recognition substance) (also referred to as a drug delivery material of the present invention). The drug delivery material of the present invention is preferably one represented by (drug-carrying molecular assembly)-(linker)-(substance recognizing activated platelet, injury site of blood vessel and/or inflammatory tissue), namely, one having these constituent arranged in this order.

In the present specification, the "drug-carrying molecular assembly" is a molecular assembly carrying a drug, and refers to a molecular assembly which, when conjugated with a linker and a recognition substance, releases the drug carried thereon at a desired cell and/or biological tissue (e.g., activated platelet, injury site of blood vessel, inflammatory tissue) but does not release the drug and does not easily exhibit the effect of the drug at other sites. Examples of such molecular assembly include a biocompatible carrier capable of parenteral administration for medical use. Examples of a preferable material of the molecular assembly include vesicle, micelle, polymer micelle, microsphere and the like. Of these, vesicle is particularly preferable.

Vesicle is a particle constituted with an artificial lipid membrane, and prepared as a lipid bilayer from phospholipid, glyceroglycolipid, cholesterol and the like. In the present invention, phospholipid bilayer vesicle is more preferable. The hydrocarbon chain constituting the lipid bilayer preferably has a carbon atom number of 12-18. It is possible to control the strength of the membrane by introducing 1 to 3 unsaturated groups into the hydrocarbon chain. When the number of carbon atoms of hydrocarbon chain is too many, the strength of the membrane becomes too high and, when a drug is carried thereon, the release of the drug becomes difficult.

In the present invention, a phospholipid bilayer vesicle constituted with a mixed lipid containing phosphatidylcholine, which is hydrogenated egg yolk lecithin, hydrogenated soybean lecithin, distearoylphosphatidylcholine or dipalmitoylphosphatidylcholine, and cholesterol (preferably essential consisting of these), more specifically, a mixed lipid containing cholesterol at a molar ratio of 20-100% relative to phosphatidylcholine, which is hydrogenated egg yolk lecithin, hydrogenated soybean lecithin, distearoylphosphatidylcholine or dipalmitoylphosphatidylcholine, is particularly preferable.

Vesicle can be prepared by a known method such as surfactant removal method, hydration method, ultrasonication method, reversed-phase distillation method, freeze-thawing method, ethanol injection method, extrusion method, and high-pressure emulsifying method and the like. The detail of the preparation of vesicle is described in JP-A-9-208599 and T. Nishiya et al., Biochim. Biophys. Res. Commun., 224, 242-245, 1996.

The particle diameter of vesicle after introduction of a linker and a recognition substance is preferably 50-300 nm, more preferably 100-270 nm, most preferably 150-250 nm, from the aspects of the introduction amounts of the linker and recognition substance, expression of their functions and pharmacokinetics. Here, the particle diameter refers to the diameter of particles after diameter control using a filter subsequent to the introduction of the linker and recognition substance. When the particle diameter becomes less than 50 nm, release of a drug carried thereon from a molecular assembly becomes difficult.

The lamellarity of the lipid bilayer vesicle is preferably 1 to 4, more preferably 1 or 2, counting the bilayer as one unit. When the lamellarity exceeds 4, release of a drug carried thereon from a molecular assembly becomes difficult.

The lamellarity can be controlled by the pore size of the filter, and dispersing medium for vesicle (pH, temperature, ionic strength). The lamellarity can be measured by freeze-fracturing, small-angle X-ray scattering method, electron spin resonance (ESR) using spin-labeled lipid, a measurement method using $^{31}$P-NMR, a measurement method using 6-p-toluidino-2-naphthalenesulfonic acid (TNS) and the like.

The drug-carrying molecular assembly is most preferably a lipid bilayer vesicle encapsulating a drug in its inner aqueous phase.

In the present specification, the "linker" is not particularly limited as long as it crosslinks a drug-carrying molecular assembly and a substance recognizing an activated platelet, an injury site of blood vessel and/or an inflammatory tissue, and has biocompatibility. As the linker, saturated or unsaturated acyclic hydrocarbon or aliphatic or aromatic cyclic hydrocarbon having a carbon number of 2-10, which has a functional group to be a binding site between a drug-carrying molecular assembly or a recognition substance, is preferable, and optionally has a hetero atom (e.g., oxygen atom, nitrogen atom and the like) on the chain or ring. In addition, two or more kinds of different linkers may be used in combination. As the linker, a compound having a functional group reactive with any of SH group, OH group, COOH group and NH$_2$ group is more preferable. Examples of the linker include those synthesized from dicarboxylic acid, aminocarboxylic acid, bismaleimide compound, bishalocarbonyl compound, halocarbonylmaleimide compound, dithiomaleimide, dithiocarboxylic acid, maleimidocarboxylic acid and the like as starting materials. Examples of the linker having a functional group reactive with any of SH group, OH group, COOH group and NH$_2$ group include those synthesized from N-α-maleimidoacetoxy)succinimide ester, N-[4-(p-azidosalicylamido)butyl]-3'-(2'-pyridyldithio)propionate, N-β-maleimidopropionic acid, N-(β-maleimidopropionic acid) hydrazide, N-(β-maleimidopropioxy)succinimide ester, N-ε-maleimidocaproic acid, N-(ε-maleimidocaproic acid)hydrazide, N-(ε-maleimidocaproyloxy)succinimide ester, N-(γ-maleimidobutyryloxy) succinimide ester, N-κ-maleimidoundecanoic acid, N-(κ-maleimidoundecanoic acid)hydrazide, succinimidyl-4-(N-maleimidomethyl)cyclohexane-1-carboxy-(6-amidocaproate), succinimidyl-6-[3-(2-pyridyldithio)-propionamido]hexanate, m-maleimidobenzoyl-N-hydroxysuccinimide ester, 4-(4-N-maleimidophenyl)butyl acid hydrazide and the like as starting materials.

The above-mentioned linker may contain, between a drug-carrying molecular assembly and a recognition substance, a spacer part capable of adjusting the length between the drug-carrying molecular assembly and the recognition substance. The position of the spacer part may be drug-carrying molecular assembly-linker-spacer-recognition substance, or drug-carrying molecular assembly-spacer-linker-recognition substance. In addition, a spacer part may be inserted between linkers which may be the same or different. That is, it may be drug-carrying molecular assembly-linker-spacer-linker-recognition substance. The spacer is not particularly limited as long as it has biocompatibility, and a substance selected from the group consisting of polyoxyethylene, polypeptide, polysaccharide, albumin and antibody can be used. As albumin and antibody, recombinants may be used. The spacer in the present invention is particularly preferably polyoxyethylene or a derivative thereof.

Examples of preferable drug delivery material of the present invention include one wherein the linker contains an amphiphilic molecule that becomes, when bound with a drug-carrying molecular assembly, a part of the constituent of the assembly, and the linker or spacer and the drug-carrying molecular assembly are bonded via the amphiphilic molecule, and one wherein the linker contains a hydrophobic molecule, and the linker or spacer and a drug-carrying molecular assembly are bound with a drug-carrying molecular assembly via the hydrophobic molecule.

Examples of the amphiphilic molecule and hydrophobic molecule include dipalmitoylphosphatidyl ethanolamine, distearoylphosphatidyl ethanolamine, dioleoylphosphatidyl ethanolamine and the like. In the present invention, Glu2C18 shown by the following formula is particularly preferable as an amphiphilic molecule.

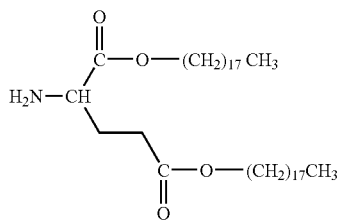

In the case of a lipid bilayer vesicle constituted with a mixed lipid containing cholesterol at a molar ratio of 20-100% relative to phosphatidylcholine, a conjugate of a linker and a substance recognizing an activated platelet, an injury site of blood vessel and/or an inflammatory tissue is preferably contained in a proportion of 0.001-20% relative to the phosphatidylcholine.

In the present specification, "a substance recognizing an activated platelet, an injury site of blood vessel and/or an inflammatory tissue" means a substance that recognizes an activated platelet, an injury site of blood vessel and/or an inflammatory tissue, directs the drug delivery material of the present invention to an activated platelet, an injury site of blood vessel and/or an inflammatory tissue, and accumulates the drug delivery material of the present invention at those sites. As the recognition substance, a substance that recognizes integrin or selectin exposed on an activated platelet, collagen exposed on an injury site of blood vessel, vWF bound with collagen exposed on an injury site of blood vessel, selectin exposed on an inflammatory tissue and/or a selectin ligand exposed on a leukocyte, and is incorporated into an aggregate of activated platelets and/or leukocytes and/or accumulated on an injury site of blood vessel and/or an inflammatory tissue is preferably used. More specifically, as a recognition substance, H12(HHLGGAKQAGDV, SEQ ID NO: 1), GPIbα, GPIa/IIa (integrinα2β1), GPVI, MAC-1, fibrinogen, P-selectin, PSGL-1 and the like are preferable.

The preparation methods of H12, GPIbα, GPIa/IIa, GPVI, MAC-1, fibrinogen, P-selectin and PSGL-1 are not particularly limited, and they can be prepared by a method including extraction or isolation from platelet membrane, a method based on cell culture, a production method by genetic engineering and the like.

As long as the object of the present invention can be achieved, the recognition substance to be used in the present invention may contain any mutation in one or plural amino acids of the amino acid sequence thereof, such as deletion, substitution, addition and modification. For example, substitute, analog, variant, modulator, derivative, glycosylated product and the like of naturally occurring recognition substances are also encompassed therein.

Examples of the GPIbα include GPIbα[His(1)-Leu(610)], GPIbα fragments such as fragments of vWF binding region of the α chain and the like, GPIbα fragments deficient in transmembrane site and the like. In the present invention, more preferred is GPIbα fragment deficient in transmembrane site.

Examples of more specific GPIbα chain include His(1)-Cys(485), His(1)-Pro(340), His(1)-Thr(304), His(1)-Ala (302), His(1)-Arg(293) [JP-A-1-221394, EP0317278], Ala (165)-Leu(184), Gln(180)-Phe(199), His(195)-Leu(214), Asn(210)-Val(229), Glu(225)-Ala(244) and Thr(240)-Tyr (259) [JP-A-1-100196], Asn(61)-Thr(75), Gln(71)-Ser(85), Thr(81)-Leu(95), Gln(97)-Arg(111), Leu(136)-Leu(150), Asn(210)-Ala(224), Gln(221)-Asp(235) and Ser(241)-Asp (255) [National Publication of International Patent Application No. H5-503708, WO91/09614] and the like. In addition, examples of the substitute include GPIbα chain fragment consisting of His(1)-Ala(302) wherein Gly(233) and Met (239) are each substituted by Val and the like [WO93/16712]. These GPIbα chain fragments are all deficient in the transmembrane site. The transmembrane site corresponds to Leu (486)-Gly(514) of GPIbα chain (Proc. Natl. Acad. Sci. USA, vol. 84, pages 5615-5619, 1987).

The drug delivery material of the present invention releases a drug from a drug-carrying molecular assembly when it reaches a cell or biological tissue, as triggered by a physical stimulation of the drug-carrying molecular assembly by the cell or biological tissue. That is, a recognition substance constituting the drug delivery material directs the drug delivery material of the present invention to a target cell or target biological tissue. When the drug delivery material of the present invention reaches the target cell or target biological tissue, the drug delivery material of the present invention interacts with the target cell or target biological tissue via a linker and a recognition substance, due to which a physical stimulation is produced and the carried drug is released from the molecular assembly. More specifically, the recognition substance is attracted to the target cell or target biological tissue, and then morphological changes of the cell or biological tissue place a physical burden on the drug-carrying molecular assembly, which degrades the drug-carrying molecular assembly to release the drug.

Here, when the target is a cell, the target is preferably an activated platelet or leukocyte. In this case, the drug delivery material is incorporated in an aggregate of activated platelets and leukocytes, and a physical stimulation due to morphological changes of platelet and leukocyte disintegrates the molecular assembly, thus causing release of the drug. When the target is a biological tissue, the target is preferably an injury site of blood vessel or an inflammatory tissue.

The number of molecules of the recognition substance to be bound on a drug-carrying molecular assembly is preferably high, since it increases the possibility of binding with a cell or biological tissue, and permits rapid formation of aggregates. The number can be adjusted appropriately by those of ordinary skill in the art, in view of the desired coagulation level and coagulation rate.

The conjugate of a drug-carrying molecular assembly, a linker, and a recognition substance can be prepared by conjugation, after preparation of the molecular assembly, the linker with the molecular assembly, and then reacting the conjugate with the recognition substance, or preparing in advance a reaction product of a linker and a recognition substance, and then binding the reaction product with a molecular assembly.

When a conjugate of a drug-carrying molecular assembly, a linker and a recognition substance wherein the linker and the drug-carrying molecular assembly are bound with the assembly via an amphiphilic molecule that becomes a part of the constituent of the assembly, or a hydrophobic molecule, is to be prepared, a reaction product of the linker, the recognition substance and the amphiphilic molecule or hydrophobic molecule may be prepared in advance, and then the reaction product may be bound with the molecular assembly.

The drug may be carried on a molecular assembly from the beginning, or finally carried on a molecular assembly after preparing a conjugate of the molecular assembly, a linker and a recognition substance. The reaction conditions can be those known per se according to the starting materials of the molecular assembly. The mixing ratio of the drug-carrying molecular assembly and the recognition substance is adjusted to meet a desired density of the recognition substance in the final conjugate.

When a conjugate of a lipid bilayer vesicle, a linker and a recognition substance wherein the linker and the lipid bilayer vesicle are bound via an amphiphilic molecule that becomes a part of the constituent of the assembly, or a hydrophobic molecule, is to be prepared, the above-mentioned amphiphilic molecule that can be a constituent of the lipid bilayer, in which the linker, the recognition substance and the amphiphilic molecule or hydrophobic molecule are bound, is mixed with a lipid constituting the vesicle in an organic solvent, and a vesicle is prepared by a conventional method to modify the surface of the vesicle with the recognition substance.

Then, where necessary, the conjugate prepared above is washed with a physiologically acceptable aqueous solution, and subjected to sterilization by filtration, dispensing and the like, whereby the drug delivery material of the present invention can be formulated into a liquid, pellet or suspension. The preparation can be formulated by a method known in the field of production of pharmaceutical products. In addition, the liquid may be frozen and vacuum dried to give a lyophilized preparation. During lyophilizing, monosaccharides (e.g., glucose etc.), disaccharides (e.g., sucrose) and the like may be added as a protector. The preparation may contain a polymer such as albumin, dextran, vinyl polymer, gelatin, hydroxylethyl starch and the like as a stabilizer. The amount of the stabilizer to be added is preferably 0.5-10 parts by weight, more preferably 1-5 parts by weight, relative to 1 part by weight of the lipid.

While the drug to be carried on the drug-carrying molecular assembly is not particularly limited as long as it exhibits a desired physiological activity in a cell such as activated platelet, leukocyte and the like, or a biological tissue such as an injury site of blood vessel, an inflammatory tissue and the like, it is preferably a platelet aggregation inducer, a platelet aggregation inhibitor, a vasoconstrictor, a vasodilator or an anti-inflammatory agent. For use as a diagnostic agent, a fluorescent reagent, a contrast agent and the like, which are free of physiological activity, may also be carried.

Examples of the platelet aggregation inducer include adenosine diphosphate (ADP), collagen, collagen-derived peptide, convulxin, serotonin, epinephrine, vasopressin, carbazochrome, blood coagulation factor (FVIII, FIX), thrombin, antiplasmin agent (e.g., ε-aminocaproic acid, tranexamic acid), protamine sulfate, ethanesylate, phytonadione, conjugated estrogen (e.g., estrone sodium sulfate, equilin sodium sulfate) and the like.

Examples of the platelet aggregation inhibitor include aspirin, dipyridamole, ticlopidine, cilostazol, beraprost, mucopolysaccharides such as heparin and the like, coumarin anticoagulant, natural extract such as hirudin and the like and derivatives thereof, physiologically active substance such as thrombomodulin, active protein C and the like, and the like. Examples of the vasoconstrictor include noradrenaline, norfenefrine, phenylephrine, metaraminol, methoxamine, prostaglandin $F_1\alpha$, prostaglandin $F_2\alpha$, thromboxane $A_2$ and the like.

Examples of the vasodilator include prostaglandin E, prostaglandin $I_2$ and the like.

Examples of the anti-inflammatory agent include steroidal anti-inflammatory agents (dexamethasone, hydrocortisone, prednisolone, betamethasone, triamcinolone, methylprednisolone and the like), non-steroidal anti-inflammatory agents (indomethacin, acemetacin, flurbiprofen, aspirin, ibuprofen, flufenamic acid, ketoprofen and the like), and the like.

As the drug to be carried on the drug-carrying molecular assembly, particularly preferred include adenosine diphosphate (ADP), collagen, collagen-derived peptide, convulxin, serotonin, aspirin, dipyridamole, ticlopidine, cilostazol and beraprost.

While it is difficult to generally define the amount of the drug to be carried on the drug-carrying molecular assembly, since it varies depending on the kind of the drug to be carried and the object of use, when, for example, the drug delivery material of the present invention is used to encapsulate ADP in a phospholipid bilayer to activate platelets at a desired site, preferably 0.1-25 mM, more preferably 0.5-10 mM, still more preferably 1-6 mM, is encapsulated in 10 mg/mL of a lipid.

While the dose of the preparation containing the drug delivery material of the present invention cannot be generally determined, since it is appropriately determined depending on the amount of the drug to be carried, gender, age, symptom of patients, and the like, for example, about 0.001-1000 mg can be administered daily. The preparation containing the drug delivery material of the present invention is preferably administered parenterally, and specifically administered by intravascular (intraarterial or intravenous) injection, continuous infusion, subcutaneous administration, topical administration, intramuscular administration and the like. The preparation containing the drug delivery material of the present invention is useful as a platelet aggregation inducer, a platelet aggregation inhibitor, a vasoconstrictor, a vasodilator and an anti-inflammatory agent, and is also useful as a pharmaceutical product such as a platelet substitute, an antiplatelet agent, an agent for the prophylaxis or treatment of vascular disorder, vascular damage, thrombosis and the like, and the like, or a diagnostic agent of platelet dysfunction syndromes such as thrombasthenia and the like, biological or medical reagent, a reagent for screening for a platelet substitute or antiplatelet agent, a diagnostic reagent for investigation or a therapeutic agent of injury site of blood vessel and angiogenesis site, and the like.

EXAMPLES

The present invention is explained in more detail in the following by referring to Examples, which are not to be construed as limitative. Unless specifically indicated in the Examples, ADP or CF encapsulation concentration shows a concentration (mM) at which ADP or CF was encapsulated in a lipid (10 mg/mL).

Example 1

ADP-Encapsulated Vesicle

1. Synthesis of Glu2C18

Glutamic acid (2.96 g, 20 mmol) and p-toluenesulfonic acid monohydrate (4.56 g, 24 mmol) were dissolved in benzene (150 mL), and the solution was refluxed at 105° C. for 1 hr while removing the generated water using a Dean-Stark trap. Stearyl alcohol (11.9 mg, 44 mmol) was added, and the mixture was further refluxed at 105° C. for 14 hr while removing the generated water. The solvent was evaporated under reduced pressure, the residue was dissolved in chloroform (150 mL), and the mixture was washed twice with saturated aqueous sodium carbonate solution (150 mL) and twice with water (150 mL). The chloroform layer was recovered, dehydrated with sodium sulfate (5 g), and the solvent was evaporated under reduced pressure. The residue was dissolved in methanol (400 mL) at 60° C. and the insoluble component, if any, was filtered off, recrystallized at 4° C., filtered and dried to give a white powder Glu2C18 (13.3 g, yield 85%).

2. Synthesis of H12-MAL-PEG-Glu2C18

Glu2C18 (115.1 mg, 176 μmol) and triethylamine (TEA) (24.6 μL, 176 μmol) were added to chloroform (5 mL), and α-maleimidyl-ω-N-hydroxysuccinimidylpolyethylene glycol (MAL-PEG-NHS) (Mw=3400) (300 mg, 58.8 μmol) was dissolved therein and the mixture was stirred at room temperature for 12 hr. The reaction solution was added dropwise to diethyl ether (250 mL), and insoluble component was collected. The collected product was dissolved in benzene and freeze-dried to give MAL-PEG-Glu2C18 as a white powder (264.8 mg, yield 64%).

MAL-PEG-Glu2C18 (n=71) (100 mg, 25.37 μmol) and the C-terminal 400-411th amino acid sequence (Cys-H12) (CHHLGGAKQAGDV, SEQ ID NO: 2) (32.8 mg, 25.37 μmol) of fibrinogen γ chain harboring cysteine at the C-terminal were dissolved in dimethylformamide (DMF) (5 mL) and the mixture was stirred at room temperature for 12 hr. The reaction solution was added dropwise to diethyl ether (250 mL), and the insoluble component was collected. Water (250 mL) was added, the insoluble component was removed, and the solvent was removed by a freeze-dryer to give a pale-yellow powder H12-MAL-PEG-Glu2C18 (62.8 mg, yield 47%).

3. Preparation Method of Vesicle

A mixed lipid (in the indication of lipid concentration in the present specification, a mixed lipid is simply indicated as a lipid) of 1,2-dipalmitoyl-sn-glycerol-3-phosphatidylcholine (DPPC) (100 mg, 136 μmol), cholesterol (52.7 mg, 136 μmol), and 1,5-dihexadecyl-N-succinyl-L-glutamate (DHSG) (19.0 mg, 13.6 μmol), and PEG-Glu2C18 (PEG-DSPE, manufactured by NOF Corporation, 4.74 mg, 0.817 μmol) or H12-MAL-PEG-Glu2C18 (4.34 mg, 0.817 μmol) were dissolved in benzene (5 mL), and the mixture was freeze-dried for 3 hr. After drying, adenosine diphosphate (ADP) solution (0, 1, 10, 25 or 100 mM) (8.5 mL) was added, and the mixture was stirred for 12 hr, and then passed through filters (3000 nm→800 nm→650 nm→450 nm→300 nm→220 nm×2) using a granulator to control the particle size. Ultracentrifugation (33000 rpm, 30 min) was performed twice and the residue was dispersed in phosphate buffered saline (PBS) (5 mL) to give a vesicle dispersion. Further, the vesicle dispersion was applied to gel filtration (Sephadex G25) to completely remove ADP remaining in a trace amount in the outer aqueous phase.

By the above-mentioned procedures, dispersions of ADP-encapsulated H12-PEG vesicle (average particle diameter 250±80 nm, average lamellarity 1.6; Glu2C18 being a part of the constituent of vesicle, hereinafter the same), ADP-unencapsulated H12-PEG vesicle (average particle diameter 230±70 nm, average lamellarity 1.8), ADP-encapsulated PEG vesicle (average particle diameter 240±90 nm, average lamellarity 1.5) and ADP-unencapsulated PEG vesicle (average particle diameter 250±90 nm, average lamellarity 1.8) were obtained.

The lipid concentration of the recovered vesicle dispersions was quantified (phospholipid C-Test Wako, manufactured by Wako Pure Chemical Industries, Ltd.) to find a lipid concentration of 18±5 mg/mL. In the below-mentioned animal experiments, the lipid concentration of each vesicle dispersion was adjusted to 0.25, 1.0, 2.5, 5.0, 10 mg/mL using PBS and the dispersion was administered at 4 mL/kg such that the lipid concentration would be 1, 4, 10, 20, 40 mg/kg (based on lipid amount).

The lamellarity (average lamellarity) of vesicle was calculated as follows.

A dispersion of ADP-unencapsulated H12-PEG vesicle (0.5 wt %, 0, 20, 30, 50, 70, 90 μL) was diluted with PBS and adjusted to a constant volume of 3 mL. TNS aqueous solution (70 μM) or pure water was added by 100 μL, and the mixture was shaken at room temperature for 12 hr. The mixture was subjected to fluorescence measurement (λex=321 nm, λem=445 nm), the proportional formula of lipid concentration and fluorescence intensity was calculated to give the slope as $K_1$. In the same manner, TNS aqueous solution (70 μM) or pure water was added to dispersions (0.5 wt %, 0, 20, 30, 50, 70, 90 μL) of PEG vesicle passed through a 0.05 μm filter. The mixture was shaken at room temperature for 12 hr and slope $K_2$ was calculated to give average number of layers $N=K_1/K_2$. The average number of layers of ADP-unencapsulated H12-PEG vesicle, ADP-encapsulated PEG vesicle and ADP-unencapsulated PEG vesicle was calculated in the same manner.

The ADP-encapsulated H12-PEG vesicle and ADP-unencapsulated H12-PEG vesicle prepared using H12-MAL-PEG-Glu2C18 are hereinafter to be indicated as H12-PEG(ADP) vesicle and H12-PEG vesicle, respectively. In addition, the ADP-encapsulated PEG vesicle and ADP-unencapsulated PEG vesicle prepared using PEG-Glu2C18 are indicated as PEG(ADP) vesicle and PEG vesicle, respectively.

4. Quantification of ADP Encapsulation Concentration Using HPLC

H12-PEG(ADP) vesicle (1 mg/mL) was solubilized with 2% lauryl ether ($C_{12}E_{10}$), and ADP was quantified by HPLC (Abs. 260 nm).

Figure 2:
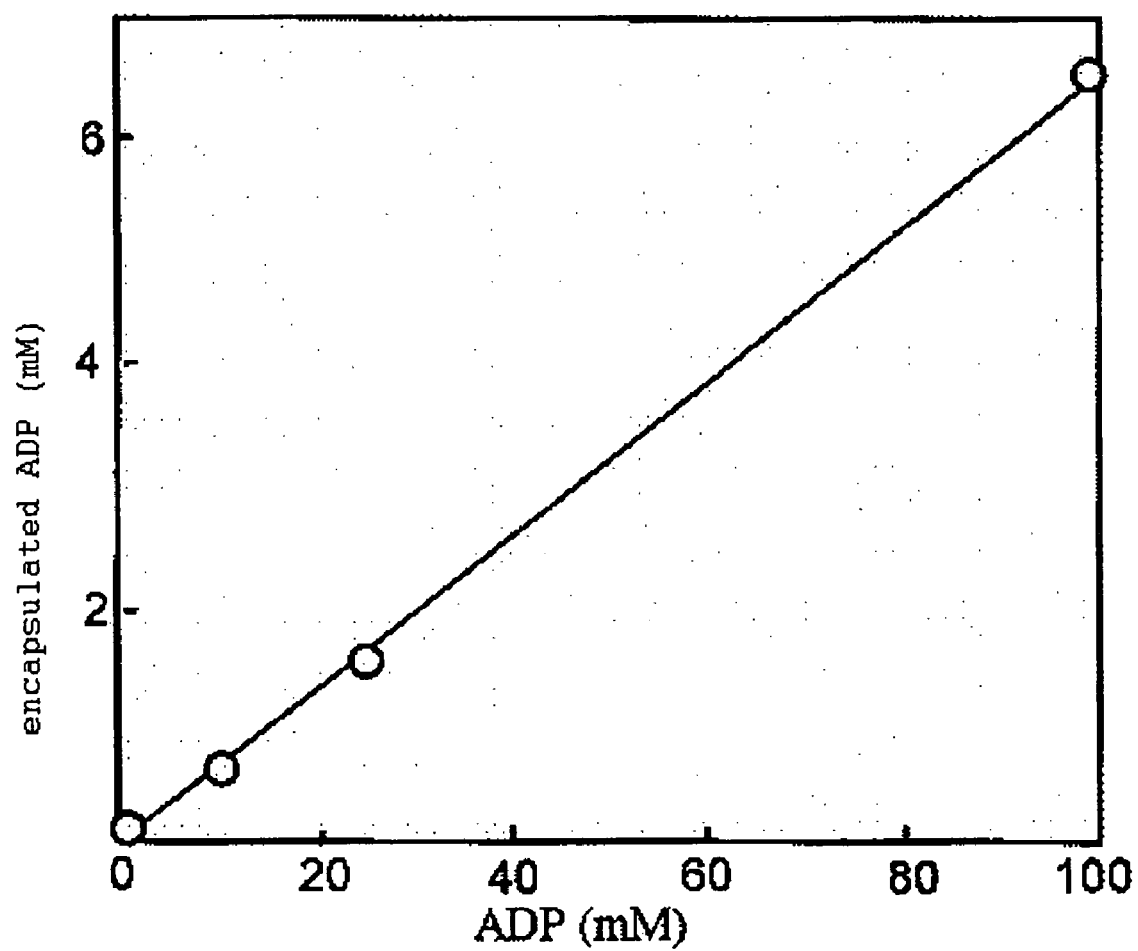
FIG. 2 shows the relationship between the concentration of ADP encapsulated in a lipid (10 mg/mL) relative to ADP concentrations in hydration (0, 10, 25, 100 mM).

The relationship between the concentration of ADP encapsulated in lipid (10 mg/mL) relative to the ADP concentration during hydration (preparation) (0, 10, 25, 100 mM) is shown in FIG. 2. It was confirmed that the concentration of encapsulated ADP was proportional to that during hydration, and that the encapsulation concentration could be controlled. Furthermore, the ADP concentration of the inner aqueous phase calculated from the particle diameter (250±80 nm) was almost equal to the ADP concentration during hydration.

5. Analysis of Interaction by Flow Cytometry (FACS)

Whole blood (1/10 (v/v) 3.8% sodium citrate) was centrifuged (600 rpm, 15 min) to give platelet rich plasma (PRP). The precipitates were further centrifuged (2500 rpm, 10 min) to give platelet poor plasma (PPP). To PRP added with PPP to adjust the number of platelets ([platelet]=$1.0\times10^5$/μL, 50 μL), H12-PEG(ADP) vesicle having a different ADP encapsulation concentration ([lipid]=1 mg/mL, 10 μL) was added, and the mixture was stirred at 37° C. for 10 min. FITC-labeled PAC-1 (20 μL), which is a platelet activation marker, was added, and the mixture was shaken at 37° C. for 10 min and fixed with formaldehyde (f.c. 1%). The sample was analyzed by flow cytometry. The positive control group was ADP-stimulated, and the negative control group was PEG vesicle.

Figure 3:
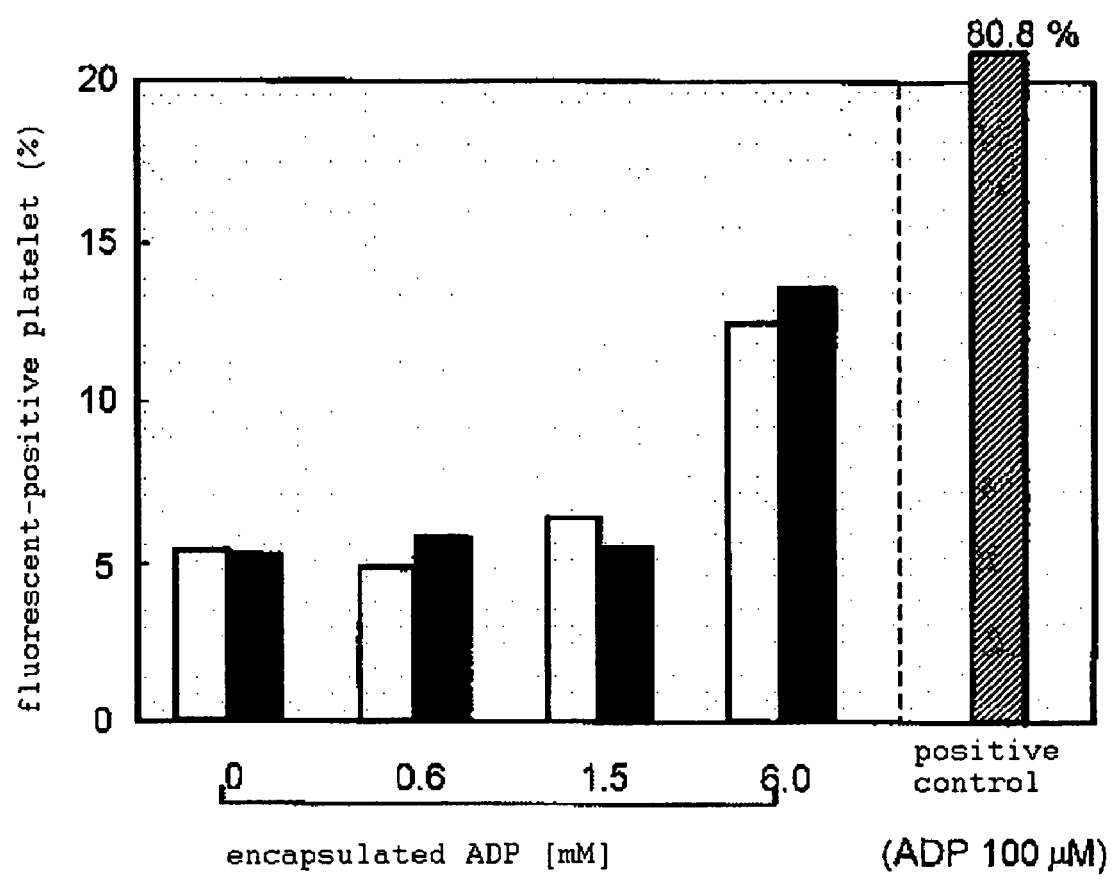
FIG. 3 shows the binding ratio of PAC-1 to platelet in the presence of H12-PEG(ADP) vesicle (black) or PEG(ADP) vesicle (white).

It was confirmed that the system, in which PEG(ADP) vesicle or H12-PEG(ADP) vesicle having an ADP encapsulation concentration of not more than 1.5 mM was added to the platelet, showed almost the same PAC-1 binding ratio as compared to the system in which ADP-unencapsulated vesicle was added, and the platelet is not activated (FIG. 3). On the other hand, it was clarified that the system, in which PEG(ADP) vesicle or H12-PEG(ADP) vesicle having the highest encapsulation concentration (6 mM) was added to the platelet, induces activation of platelet.

6. Functional Evaluation by Aggregometer

Figure 4:
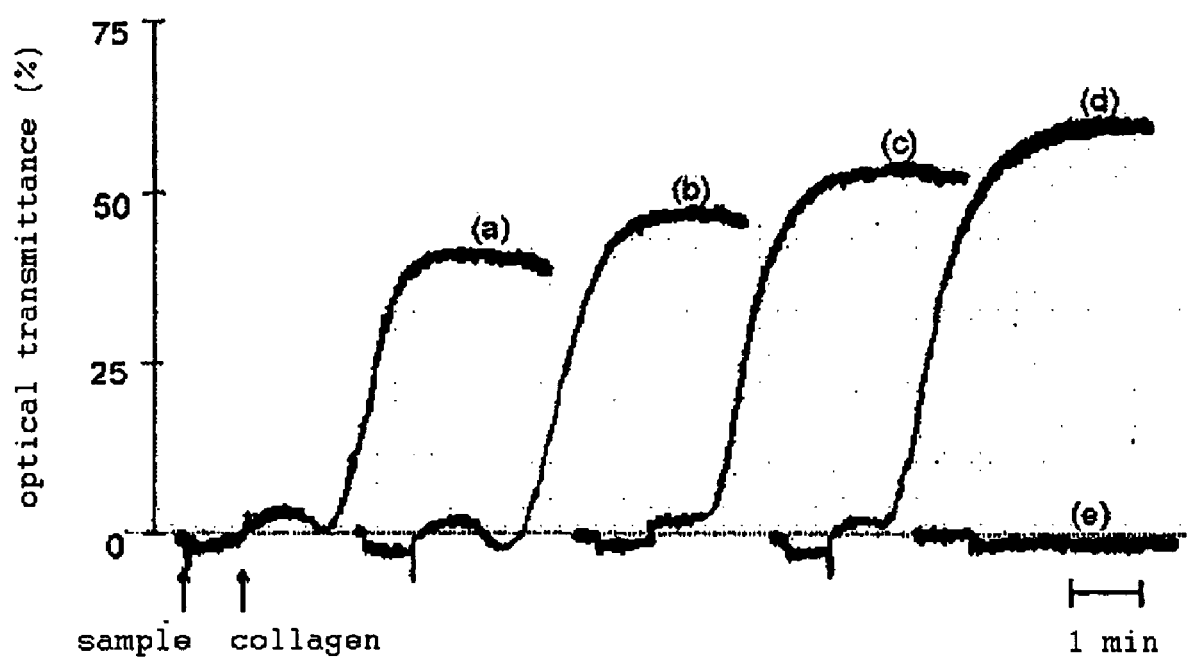
FIG. 4 shows changes in the transmittance showing the promoting effect on collagen-induced platelet aggregation by H12-PEG(ADP) vesicle. [collagen]: f.c. 0.4 µg/mL, [platelet]: $2.0 \times 10^5$/µL, [lipid]: 0.05 mg/mL. (a) PEG vesicle, (b) H12-PEG vesicle, (c) PEG(ADP) vesicle, (d) H12-PEG (ADP) vesicle, (e) collagen in the absence of H12-PEG(ADP) vesicle.

In the following experiment, PEG(ADP) vesicle and H12-PEG(ADP) vesicle clarified to not activate the platelets by FACS measurement and having an ADP encapsulation concentration of 1.5 mM, as well as PEG vesicle and H12-PEG vesicle were used. To PRP ([platelet]=$2.0\times10^5$/μL, 180 μL) adjusted in the number of platelets with PPP vesicle dispersion (10 μL) was added, platelet aggregation was induced by collagen (f.c. 0.4 μg/mL, 10 μL) and changes in the transmittance were measured (FIG. 4).

It was confirmed that addition of PEG vesicle (a) did not affect platelet aggregation as compared to the system added with PBS. When H12-PEG vesicle (b) was added instead of PEG vesicle (a), the transmittance increased and a platelet aggregation-promoting effect was confirmed. This is considered to be attributable to multipoint binding of H12-PEG vesicle with platelets to promote platelet aggregation. The aggregation was promoted in PEG(ADP) vesicle (c) as compared to (b), and H12-PEG(ADP) vesicle (d) showed more than the promoting effect of (c). On the other hand, it was confirmed that mere presence of (d) (namely, in the absence of collagen, (e)) does not induce aggregation of platelets. Thus, it is assumed that collagen induced platelet aggregation, and vesicle was immediately incorporated in the aggregates physically and deformed to release ADP. The effect of (d) is considered to have resulted from the synergistic effect of multipoint binding and ADP release, due to the presence of H12 carried thereon.

Further, about 1 min after collagen addition, a gradual decrease in the transmittance, which is associated with platelet deformation due to collagen stimulation, can be seen ((a) and (b)). However, in ADP encapsulation systems (c) and (d), the transmittance increased immediately after collagen addition, which is characteristic of ADP stimulation. From this, it is suggested that platelet aggregation induced release of ADP from H12-PEG(ADP) vesicle (d).

7. Evaluation of Influence of H12-PEG Vesicle and H12-PEG (ADP) Vesicle on Tail Bleeding Time Using Thrombocytopenia Model Rat Busulfan (20 mg/kg) was administered to male Wistar rats (8-week-old, 250-270 g) from the tail vein and the rats at day 10 from the administration were used as thrombocytopenia model rats ([platelet]=$20\times10^4$/μL). Under sevoflurane anesthesia, samples were administered. At 5 min after the administration, a cut of 2.5 mm length and 1 mm in depth was made at 1 cm from the tail tip. The cut was immersed in saline and the bleeding time was measured.

Figure 5:
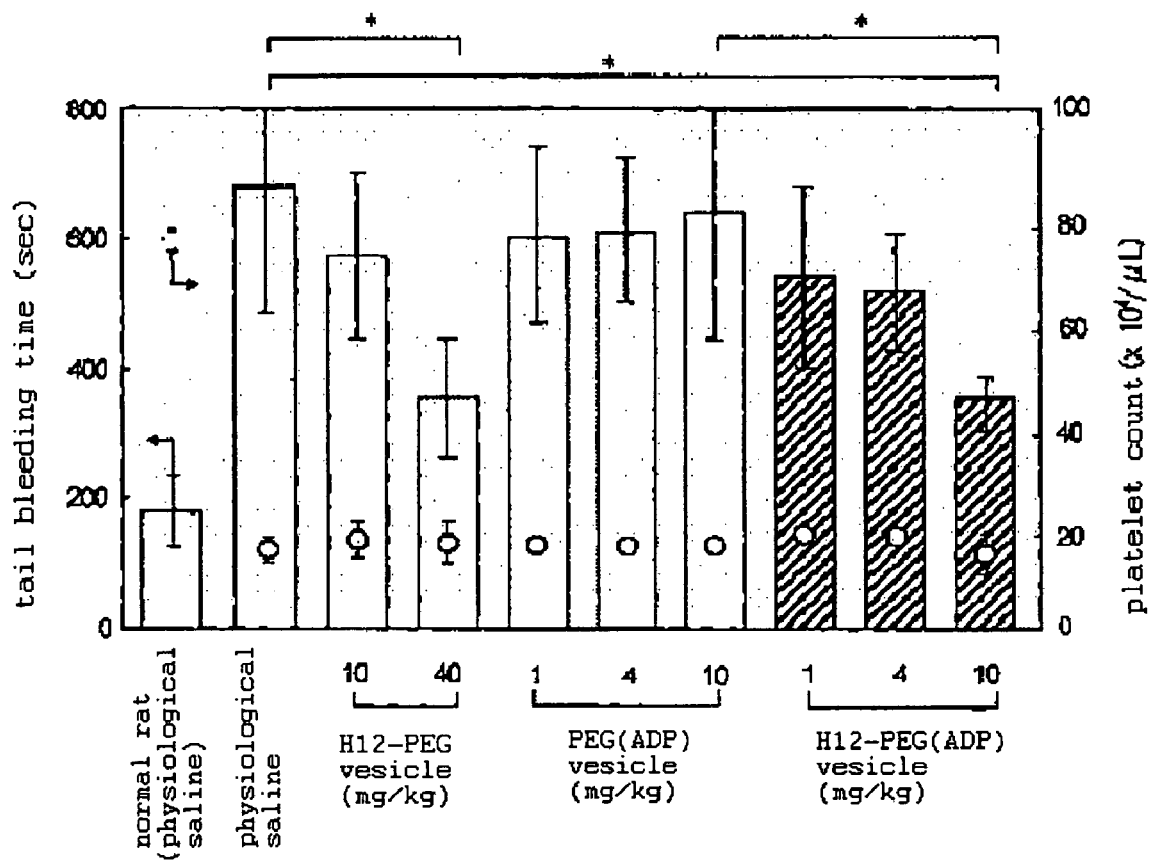
FIG. 5 shows the hemostatic effect of administration of H12-PEG(ADP) vesicle on tail bleeding time. dose of H12-PEG(ADP) vesicle: 1, 4, 10 mg/kg (based on lipid content). ○: platelet counts (N=10). *P<0.05.

When saline (4 mL/kg) was administered to the thrombocytopenia model rats, the bleeding time was 682±198 seconds, which was about 3.8 times longer than that (178±56 seconds) of normal rats ([platelet]=$80\times10^4$/μL) (FIG. 5). When H12-PEG vesicle dispersions having lipid concentrations adjusted to 2.5, 10 mg/mL were administered (4 mL/kg), the bleeding times were shortened in a dose-dependent manner and were 573±127 and 335±96 seconds for 10, 40 mg/kg (based on lipid amount), respectively. When H12-PEG(ADP) vesicle dispersions (ADP encapsulation concentration 1 mM) having lipid concentrations adjusted to 0.25, 1, 2.5 mg/mL were administered (4 mL/kg), the bleeding times for 1, 4, 10 mg/kg (based on lipid amount) were 543±134, 521±88, 349±49 seconds, respectively. Thus, it was clarified that the bleeding time can be shortened with ¼ of the administration amount confirmed to provide the shortening effect in H12-PEG vesicle. From the above, an improvement in the hemostatic effect of H12-PEG vesicle by ADP encapsulation was confirmed in vivo.

8. Evaluation of Influence of H12-PEG(ADP) Vesicle on Ear Bleeding Time Using Severe Thrombocytopenia Model Rabbits Busulfan (30 mg/kg) was administered to New Zealand white rabbits (11-week-old, 2.5 kg) from the tail vein and the rabbits at day 15 from the administration were used as thrombocytopenia model rabbits ([platelet]=$2.6\times10^4$ μL). Under ketamine/Celactal anesthesia, samples were administered at a rate of 0.5 mL/min. At 30 min after the administration, a cut of 6 mm length was made on the auricular peripheral vein. The cut was immersed in saline and the bleeding time was measured.

Figure 6:
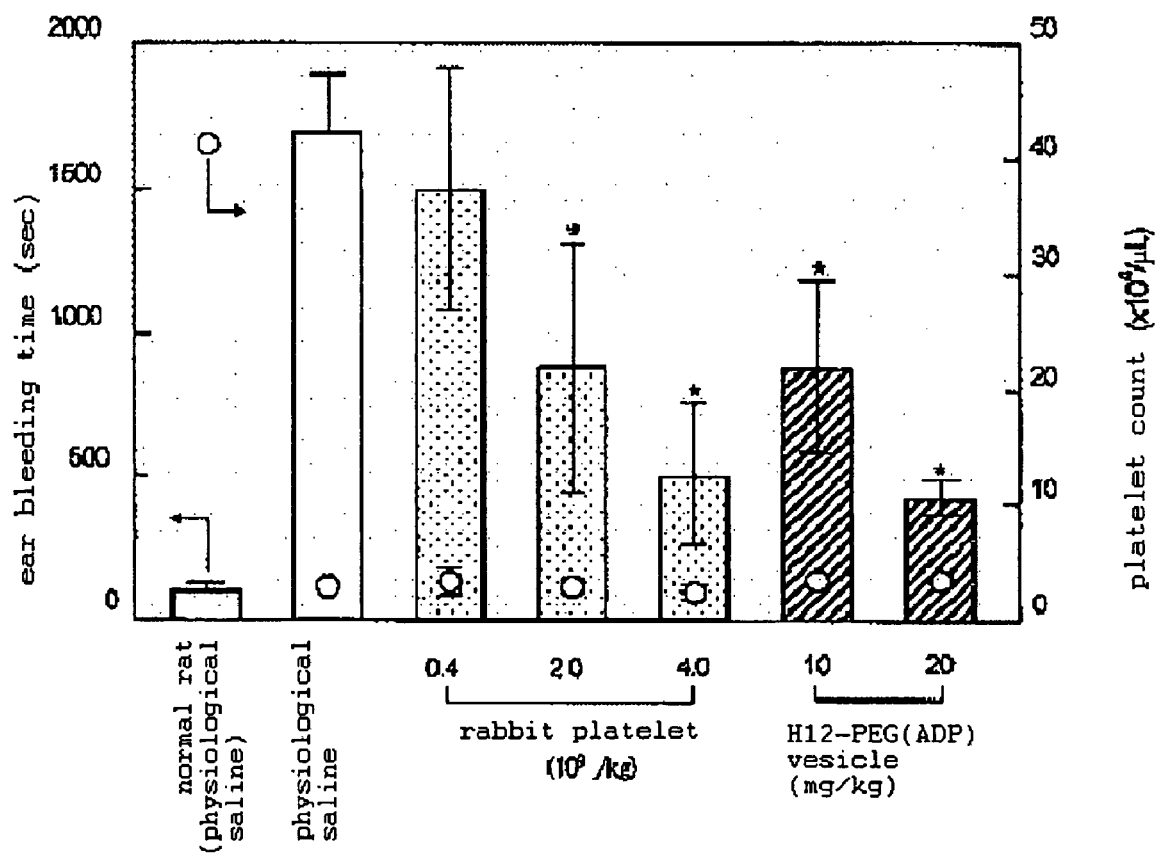
FIG. 6 shows the hemostatic effect of administration of H12-PEG(ADP) vesicle and PRP on ear bleeding time. dose of H12-PEG(ADP) vesicle: 10, 20 mg/kg (based on lipid content). dose of rabbit platelet: 0.4, 2.0, $4.0 \times 10^9$/kg. ○: platelet counts (N=5-6). P<0.05 vs. saline group.

When saline (4 mL/kg) was administered to the thrombocytopenia model rabbits, the bleeding time was 1695±197 seconds, which was about 15 times longer than that (112±24 seconds) of normal rabbits ([platelet]=$41\times10^4$/μL) (FIG. 6). As a positive control group, rabbit platelets were administered at $0.4\times10^9$, $2.0\times10^9$, $4.0\times10^9$/kg and the bleeding time was shortened in a dose-dependent manner (1505±410, 863±440, 505±257 seconds, respectively). When H12-PEG (ADP) vesicle dispersions having lipid concentrations adjusted to 2.5, 5.0 mg/mL were administered (4 mL/kg), the bleeding times were 881±303, 433±52 seconds, respectively. Thus, the bleeding time was significantly shortened in a dose-dependent manner as compared to the saline group, which was comparable to that of the platelets administration group. Hence, H12-PEG(ADP) vesicle was confirmed to efficiently shorten the bleeding time of thrombocytopenia model rabbits.

Figure 7:
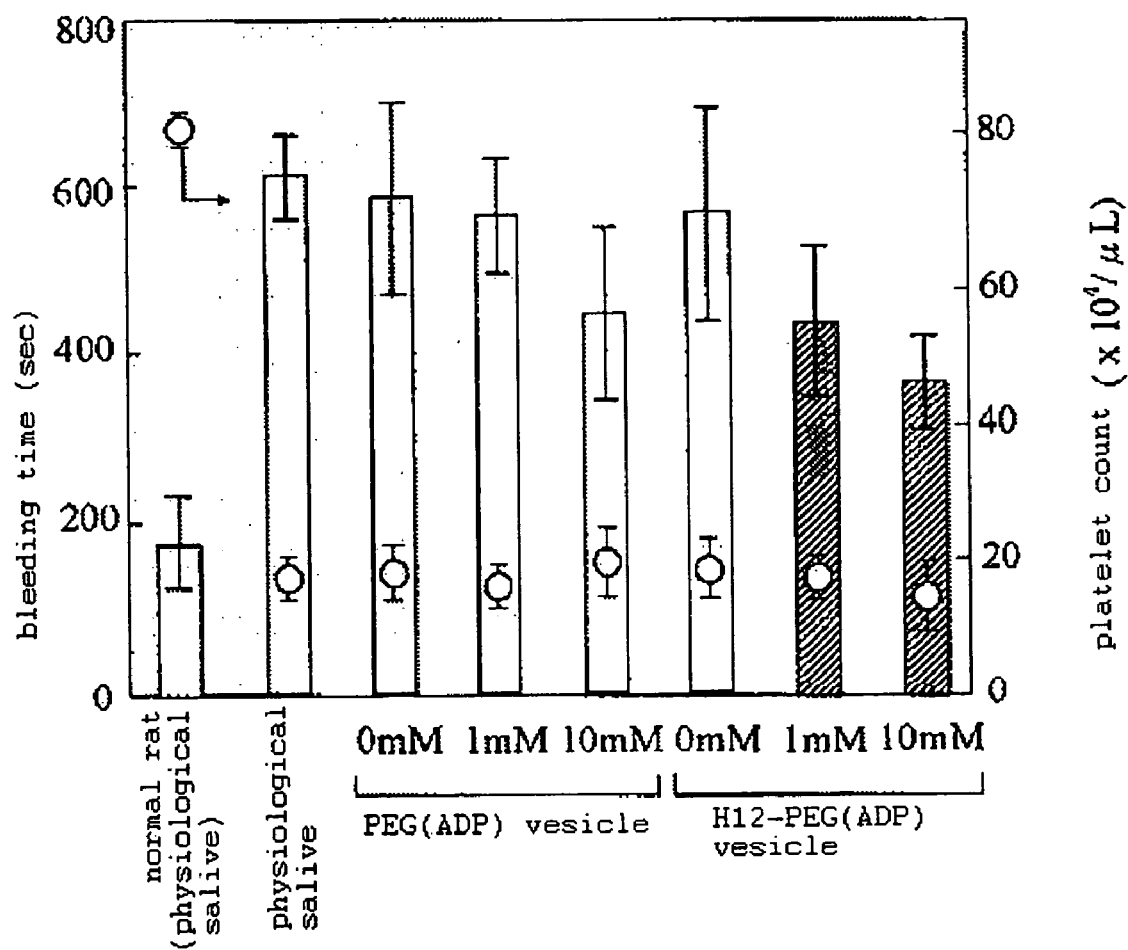
FIG. 7 shows a comparison of hemostatic effects of PEG (ADP) vesicle and H12-PEG(ADP) vesicle on tail bleeding time. dose of vesicle: 10 mg/kg. ○: platelet counts (N=6-10).
Figure 8:
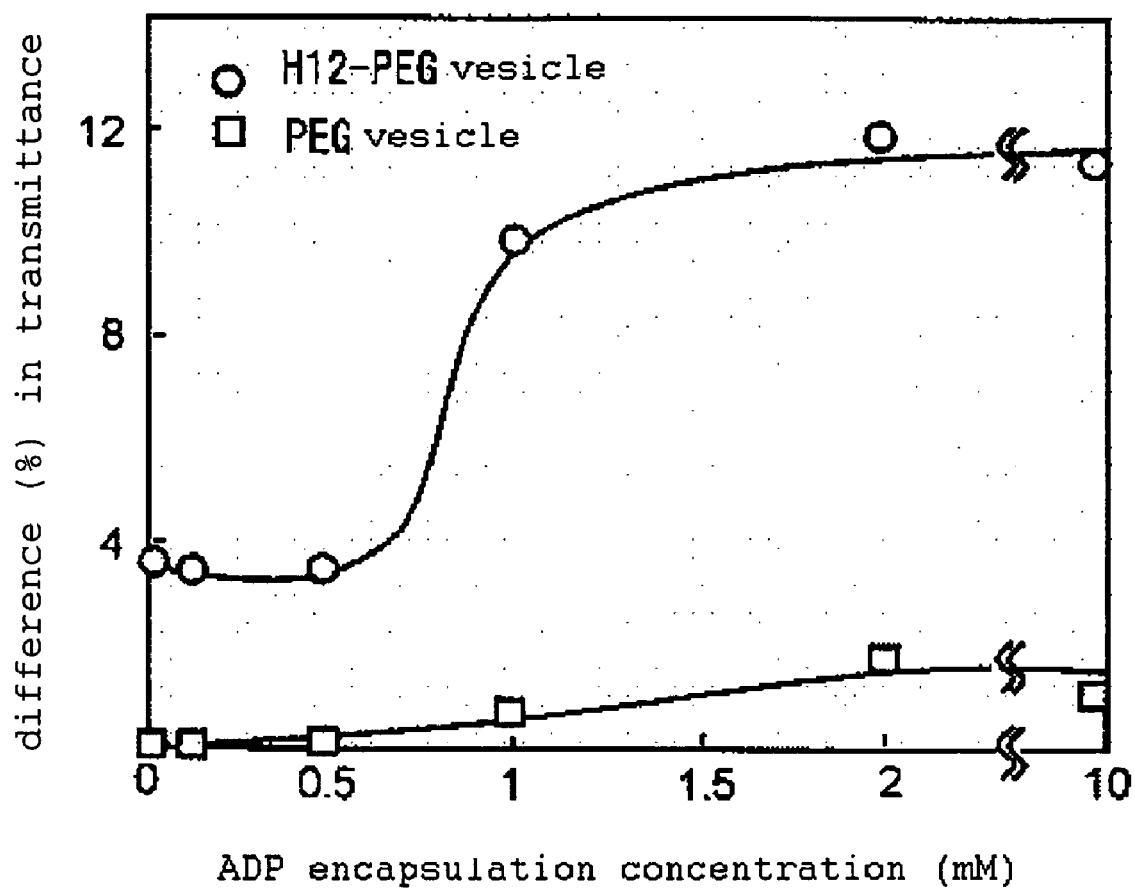
FIG. 8 shows the effect of encapsulation of ADP in PEG vesicle and H12-PEG vesicle.

9. Comparison of Influence of PEG(ADP) Vesicle and H12-PEG(ADP) Vesicle on Bleeding Time Dispersions (10 mg/kg (based on lipid amount), ADP encapsulation concentration 0, 1, 10 mM) of PEG(ADP) vesicle or H12-PEG(ADP) vesicle were administered and the bleeding times were measured. The bleeding times were measured in the same manner as in 7. using healthy rats and thrombocytopenia model rats. The results are shown in FIG. 7. In the H12-PEG vesicle (namely, ADP encapsulation concentration 0) administration, a bleeding time-shortening effect was not seen. However, a significant shortening of bleeding time was observed in H12-PEG(ADP) vesicle as compared to the saline administration to thrombocytopenia model rats and a comparable level of shortening was available with 1/10 of the administration amount confirmed to provide the shortening effect in PEG(ADP) vesicle. From the above, it was confirmed that H12-PEG(ADP) vesicle exhibits a more superior hemostatic effect to PEG(ADP) vesicle 10. Measurement of ADP Encapsulation Effect Using Aggregometer Regarding PEG vesicle and H12-PEG vesicle, with different ADP encapsulation amounts (PEG(ADP) vesicle, H12-PEG(ADP) vesicles) were prepared. The ADP encapsulation concentrations were quantified by solubilizing vesicles with 2% lauryl ether and applying same to HPLC (260 nm). The ADP encapsulation effects were evaluated by an aggregometer. Platelet-reduced plasma (PLT)((platelet)=$10\times10^4$/μL, 180 μL) having the number of platelets adjusted with PPP was prepared, vesicle dispersions (10 μL) were added, then ADP (30-45 µM, 10 µL) was added and the transmittance was measured. As the vesicle added, PEG(ADP) vesicle or H12-PEG(ADP) vesicle having an ADP encapsulation concentration of 0, 0.1, 0.5, 1.0, 2.0 or 10.0 mM was used. The evaluation was based on the difference from the transmittance with addition of PEG vesicle. The results with platelet aggregation induced by ADP are shown in FIG. 8. In the H12-PEG(ADP) vesicle addition, an encapsulation effect could be confirmed with an ADP encapsulation concentration of not less than 1 mM, and the encapsulation effect was almost the same for encapsulated vesicle having a higher concentration. The encapsulation effect could not be confirmed in the PEG (ADP) vesicle addition.

11. Synthesis of Bio-PEG-Glu2C18

N-[6-(Biotinamide)hexyl]-3'-(2'-pyridyldithio)propionamide (Bio-HPDP, 10 mg, 18.5 µmol) was dissolved in DMF (5 mL), aqueous dithiothreitol solution (1M, µL) was added, and the mixture was stirred at room temperature for 30 min. MAL-PEG-Glu2C18 (73.0 mg, 18.5 µmol) was added and the mixture was stirred at room temperature for 12 hr. The reaction solution was added dropwise to diethyl ether (250 mL) and insoluble component was collected. Water (250 mL) was added, the insoluble component was removed and the solvent was removed by a freeze-dryer to give a pale-yellow powder Bio-MAL-PEG-Glu2C18 (Bio:biotin).

Figure 9:
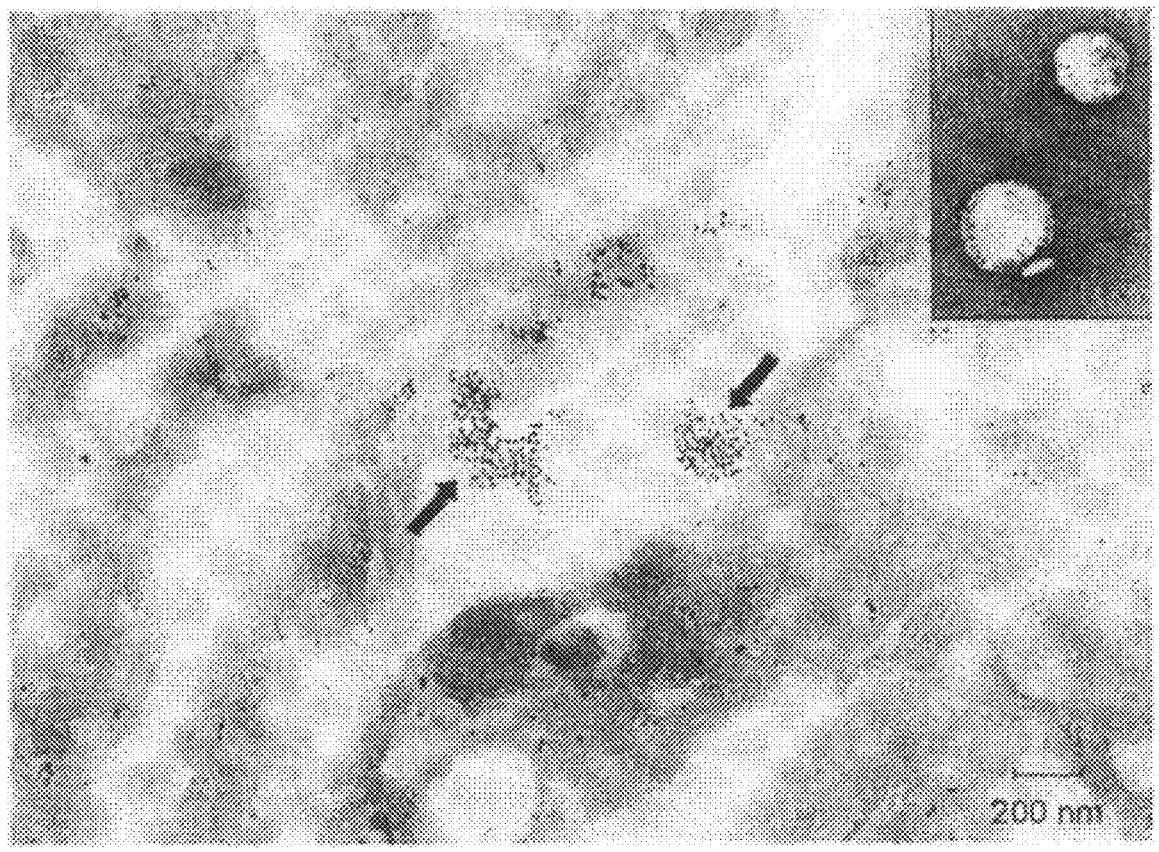
FIG. 9 shows transmission electron microscopic image of platelet aggregation, wherein an arrow indicates H12-PEG (ADP) vesicle.

12. Electron Microscopic Observation of H12-PEG(ADP) Vesicle Incorporated in Platelet Aggregates For the purpose of observing vesicle in H12-PEG(ADP) vesicle addition system, Bio-MAL-PEG-Glu2C18 was introduced into H12-PEG(ADP) vesicle. The aggregates were lyophilized and ultrathin-sectioned and observed immunocytochemically using a transmission electron microscope (FIG. 9). Since vesicles incorporated between platelets were confirmed, and Bio-MAL-PEG-Glu2C18s were scattered in each site of the platelet, disintegration of vesicle in the aggregates were suggested.

Example 2

CF-encapsulated Vesicle

1. Production of CF-encapsulated PEG Vesicle and CF-encapsulated H12-PEG Vesicle According to the steps described in Example 1, 1.-3., PEG vesicle and H12-PEG vesicle encapsulating 5(6)-carboxy fluorescein (CF, 10 mM) were produced. The amount of encapsulated CF was quantified in the same manner as in Example 1, 4.

CF-encapsulated PEG vesicle (average particle diameter 230±80 nm, average lamellarity 1.8)

CF-encapsulated H12-PEG vesicle (average particle size 240±50 nm, average number of layers 1.6)

2. Quantification of Amount of Vesicle Encapsulation Product Released in Association with Platelet Aggregation CF (10 mM)-encapsulated PEG vesicle or CF (10 mM)-encapsulated H12-PEG vesicle was added to PRP ([platelet]= $2.0 \times 10^5$ µL, [vesicle]=f.c. 0.05 mg/mL), platelet aggregation was induced by ADP ([ADP]=f.c. 2 µM), and changes in the transmittance was measured using an aggregometer. After the completion of the measurement, the aggregation cluster was removed by centrifugation (1200 rpm, 5 min). Here, the platelet alone was removed from the ADP non-addition system, and the fluorescence intensity (A) when vesicle was solubilized with 2% lauryl ether ($C_{12}E_{10}$) was measured and defined to be 100%. The Fluorescence intensity (B) of the supernatant (vesicle dispersion) was measured, and vesicle incorporation ratio into the platelet aggregation cluster was calculated. Furthermore, the supernatant was centrifuged (33000 rpm, 45 min) to remove vesicle, the fluorescence intensity (C) of the supernatant was measured, and the CF release ratio from vesicle incorporated into the platelet aggregates were calculated.

$$\text{vesicle incorporation ratio (\%)} = \frac{(A-B)}{A} \times 100$$

$$\begin{array}{l}\text{CF release ratio from vesicles}\\ \text{incorporated into platelet}\\ \text{aggregation cluster (\%)}\end{array} = \frac{C}{(A-B)} \times 100$$

Figure 10:
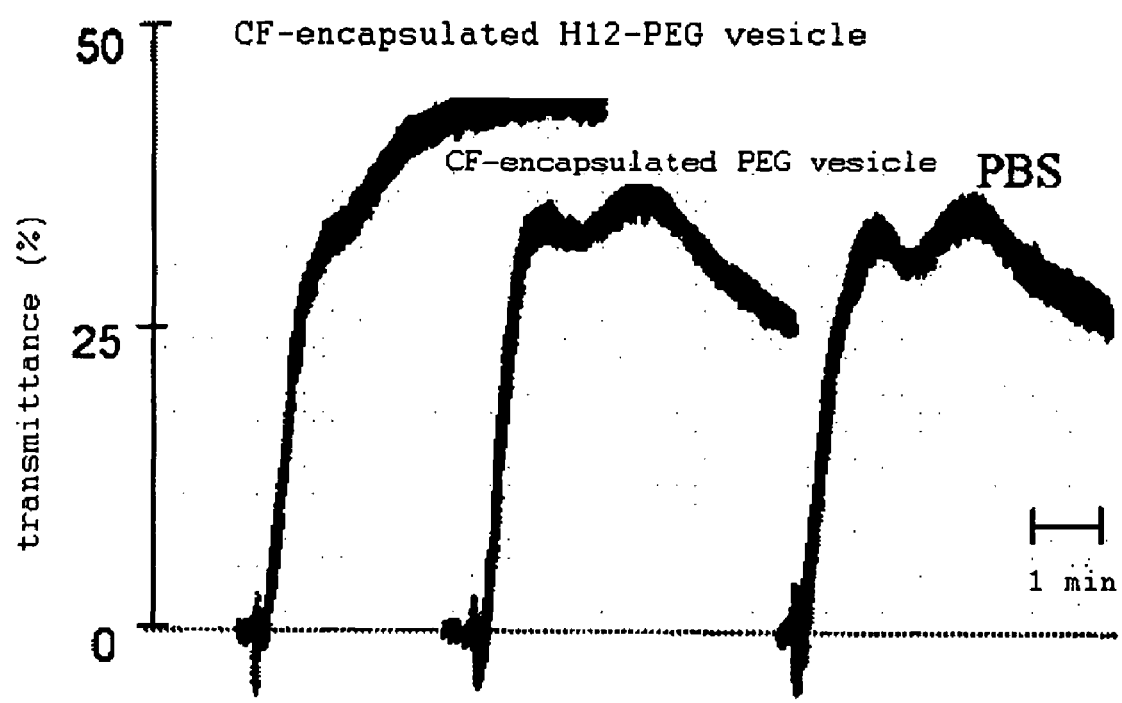
FIG. 10 shows changes in the transmittance showing the promoting effect on ADP-induced platelet aggregation of CF-encapsulated H12-PEG vesicle.

It was confirmed that addition of CF-encapsulated PEG vesicle does not affect platelet aggregation at all, as compared to a system added with PBS. When CF-encapsulated H12-PEG vesicle was added instead of CF-encapsulated PEG vesicle, secondary coagulation was promoted and the transmittance increased. Thus, a platelet aggregation-promoting effect was confirmed (FIG. 10). This is considered to be attributable to multipoint binding of CF-encapsulated H12-PEG vesicle with platelet, which promoted platelet aggregation.

The incorporation ratio of CF-encapsulated PEG-vesicle and CF-encapsulated H12-PEG vesicle into the platelet aggregation cluster were 13±5 and 17±5%, respectively, and the both were almost equivalent. Thus, the CF release ratios from the incorporated vesicle were measured to find 0.6±0.5 and 10±1% (Table 1). This is considered to be attributable to strong binding of vesicle and platelet due to H12 carried on the vesicle, and increased CF release ratio due to physical stimulation during incorporation of the vesicle into platelet aggregation.

TABLE 1

Vesicle incorporation ratio and CF release ratio due to platelet aggregation

|  | Incorporation ratio (%) | CF release ratio (%) |
|---|---|---|
| CF-encapsulated PEG vesicle | 13 ± 5 | 0.6 ± 0.5 |
| CF-encapsulated H12-PEG vesicle | 17 ± 5 | 10 ± 1 |

[platelet] = $2.0 \times 10^5$/µL,
[ADP] = f.c.2 µM,
[lipid] = f.c.0.05 mg/mL

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

This application is based on a patent application No. 2006-001916 filed in Japan, the contents of which are incorporated in full herein by this reference.

INDUSTRIAL APPLICABILITY

The drug delivery material of the present invention shows selective bindability with an activated platelet, an injury site of blood vessel and/or an inflammatory tissue, and releases a carried drug only at these sites. Therefore, the effect of the carried drug can be expressed only at an activated platelet, an injury site of blood vessel and/or an inflammatory tissue, without adversely affecting the non-desired sites. Accordingly, a preparation containing the drug delivery material of the present invention is useful as a platelet aggregation inducer, a platelet aggregation inhibitor, a vasoconstrictor, a vasodilator and an anti-inflammatory agent, and is also useful as a pharmaceutical product such as a platelet substitute, an antiplatelet agent, an agent for the prophylaxis or treatment of vascular disorder, vascular injury, thrombosis and the like, and the like, or a diagnostic agent of platelet dysfunction syndromes such as thrombasthenia and the like, biological or medicinal reagent, a reagent for screening for a platelet substitute or antiplatelet agent, a diagnostic reagent for investigation or a therapeutic agent for injury site of blood vessel and angiogenesis site, and the like.

SEQUENCE LISTING FREE TEXT

SEQ ID NO: 1: design peptide
SEQ ID NO: 2: design peptide

3. The drug delivery material of claim 1, which is represented by (a drug encapsulating vesicle)—(a linker)—(a substance that recognizes an activated platelet and/or a injury site of blood vessel.

4. The drug delivery material of claim 3, wherein the linker comprises an amphiphilic molecule that becomes a part of the constituent of the vesicle when bound therewith, and the linker is bound with the vesicle via said amphiphilic molecule.

5. The drug delivery material of claim 3, wherein the linker comprises a hydrophobic molecule, and the linker and the vesicle are bound with the vesicle via said hydrophobic molecule.

6. The drug delivery material of claim 1, wherein the linker comprises a spacer part.

7. The drug delivery material of claim 6, wherein the spacer part is polyoxyethylene.

8. The drug delivery material of claim 2, wherein the lipid bilayer vesicle consists of a mixed lipid comprising cholesterol in a molar ratio of 20-100% relative to phosphatidylcholine, which is hydrogenated egg yolk lecithin, hydrogenated soybean lecithin, distearoyl phosphatidylcholine or dipalmi-

The invention claimed is:

1. A drug delivery material which is a conjugate of 1) a drug encapsulating vesicle, 2) a linker and 3) a substance that recognizes an activated platelet and/or an injury site of blood vessel, wherein the drug is adenosine diphosphate and is encapsulated at a concentration of 1-6 mM in 10 mg/ml of a lipid constituting the vesicle, and wherein the substance that recognizes the activated platelet and/or the injury site of the blood vessel is selected from the group consisting of H12, GPIbα, GPIa/IIa, GPVI, MAC-I and fibrinogen.

2. The drug delivery material of claim 1, wherein the vesicle is a lipid bilayer vesicle encapsulating the drug in an inner aqueous phase thereof.

toyl phosphatidylcholine, and the conjugate of the linker and the substance that recognizes an activated platelet and/or a injury site of blood vessel in a proportion of 0.001-20% relative to the phosphatidylcholine.

9. The drug delivery material of claim 8, wherein the lipid bilayer vesicle has a particle diameter of 50-300 nm, and the lamellarity of the lipid bilayer is 1 to 4.

10. The drug delivery material of claim 1, wherein the drug is released from the drug encapsulating vesicle with a physical stimulation from a cell or biological tissue when it reaches the cell or biological tissue.

11. The drug delivery material of claim 10, wherein the cell is an activated platelet.

12. The drug delivery material of claim 10, wherein the biological tissue is a injury site of blood vessel.

13. A diagnostic agent comprising the drug delivery material of claim 1.

14. A reagent comprising the drug delivery material of claim 1.

15. A platelet aggregation inducer comprising the drug delivery material of claim 1.

16. A diagnostic agent comprising the drug delivery material of claim 10.

17. A reagent comprising the drug delivery material of claim 10.

18. A platelet aggregation inducer comprising the drug delivery material of claim 10.

19. The drug delivery material of claim 1, wherein the adenosine diphosphate is encapsulated in a concentration of 1-2 mM in 10 mg/mL of a lipid constituting the vesicle.

20. The drug delivery material of claim 10, wherein the adenosine diphosphate is encapsulated in a concentration of 1-2 mM in 10 mg/mL of a lipid constituting the vesicle.

21. A method of delivering a drug, comprising administering the drug delivery material of claim 1 to a mammal.

* * * * *

```
                              SEQUENCE LISTING

<160> NUMBER OF SEQ ID NOS: 2

<210> SEQ ID NO 1
<211> LENGTH: 12
<212> TYPE: PRT
<213> ORGANISM: Artificial
<220> FEATURE:
<223> OTHER INFORMATION: Synthetic Construct; Designed Peptide

<400> SEQUENCE: 1

His His Leu Gly Gly Ala Lys Gln Ala Gly Asp Val
1               5                   10

<210> SEQ ID NO 2
<211> LENGTH: 13
<212> TYPE: PRT
<213> ORGANISM: Artificial
<220> FEATURE:
<223> OTHER INFORMATION: Synthetic Construct; Designed Peptide

<400> SEQUENCE: 2

Cys His His Leu Gly Gly Ala Lys Gln Ala Gly Asp Val
1               5                   10
```